United States Patent [19]
Camus et al.

[11] Patent Number: 6,021,210
[45] Date of Patent: Feb. 1, 2000

[54] IMAGE SUBTRACTION TO REMOVE AMBIENT ILLUMINATION

[75] Inventors: Theodore A. Camus, Mount Laurel, N.J.; Thomas A. Chmielewski, Jr., Langhorne, Pa.

[73] Assignee: Sensar, Inc., Moorestown, N.J.

[21] Appl. No.: 08/980,989

[22] Filed: Dec. 1, 1997

[51] Int. Cl.[7] .............................. G06K 9/00; H04N 5/222; H04N 5/14
[52] U.S. Cl. ............................ 382/117; 348/370; 348/701
[58] Field of Search ..................................... 348/131, 164, 348/227, 366, 370, 602, 701, 132, 68, 69, 70; 250/214 AL, 214 B, 208.1

[56] References Cited

U.S. PATENT DOCUMENTS

| 4,490,037 | 12/1984 | Anagnostopoulos et al. | 356/1 |
| 4,636,850 | 1/1987 | Stewart | 358/111 |
| 4,641,349 | 2/1987 | Flom et al. | 382/2 |
| 5,291,560 | 3/1994 | Daugman | 382/2 |
| 5,497,430 | 3/1996 | Sadovnik et al. | 382/156 |
| 5,574,511 | 11/1996 | Yang et al. | 348/586 |

FOREIGN PATENT DOCUMENTS

| 42 28 629 A1 | 3/1994 | Germany | H04N 51/33 |
| 9-305765 | 11/1997 | Japan | G06T 7/00 |
| WO 94/26057 | 11/1994 | WIPO | H04N 1/00 |

*Primary Examiner*—Leo H. Boudreau
*Assistant Examiner*—Shawn B. Cage
*Attorney, Agent, or Firm*—Buchanan Ingersoll, P.C.

[57] ABSTRACT

In a method of image subtraction a series of frames of a subject are taken using a video camera The subject is illuminated in a manner so that illumination is alternately on then off for successive fields within the image frame. A single frame is grabbed and an absolute difference between the odd field and the even field within that single image frame is determined. The resulting absolute difference image will represent the subject as illuminated by the system illumination only, and not by any ambient illumination, and can then be used to identify the subject in the image.

8 Claims, 4 Drawing Sheets

IMAGE SUBTRACTION TO REMOVE AMBIENT ILLUMINATION

BACKGROUND OF THE INVENTION

1. Field of the Invention

The invention relates to a method for removing ambient illumination from an image to allow further processing or analysis of the image.

2. Background of the Invention

There are several methods known as biometrics for recognizing or identifying an individual. These methods include analyzing a signature, obtaining and analyzing an image of a fingerprint and imaging and analyzing the retinal vascular patterns of a human eye. Recently the art has used the iris of the eye which contains a highly detailed pattern that is unique for each individual and stable over many years as a non-contact, non-obtrusive biometric. This technique is described in U.S. Pat. No. 4,641,349 to Flom et al. and U.S. Pat. No. 5,291,560 to Daugman. The iris identification techniques disclosed by Flom and Daugman require a clear, well-focused image of the iris portion of the eye. Once that image is obtained a comparison of that image with a coded file image of the iris of the person to be identified can be accomplished quite rapidly. However, prior to the present invention there has not been an optical system which could rapidly acquire a sufficiently clear image of an iris of the person to be identified unless that person positioned his eye in a fixed position relatively close to an imaging camera. In a commercial embodiment of this iris identification the user is required to position his eye on an eyepiece. This provides an advantage in that the eyepiece eliminates the effects of ambient lighting. It also eliminates the necessity of automatic iris image acquisition, since the subjects themselves are responsible for positioning their own eyes at the proper location for the device to function. However, the device is impractical for users of automated teller machines and for other situations in which an individual must be rapidly and unobtrusively identified. Yet, when one allows the person to be identified to stand away from the camera lens, ambient lighting conditions such as background lighting can confuse and distract the process of automatic iris acquisition, depending on the algorithms used. In addition, lighting from around the subject may obscure portions of the image or create artifacts that prevent identification.

It has been known for many years that the effects of lighting could be removed by taking two images, one while the illuminator is on and the second while the illuminator is off. Then a pixel by pixel comparison is made between the two images. Usually this has involved subtraction of the gray scale values for corresponding pixels in the two images. Sometimes pixel values have been enhanced by multiplication of the gray scale values or by other mathematical operations. Furthermore, the illuminators could generate visible light, infrared light beams or even X-rays to create the image. Examples of such prior art image subtraction are contained in U.S. Pat. Nos. 4,636,850 and 4,490,037.

One problem with the prior art image subtraction methods is that one must know which of the two images was made while the illuminators were on and which was made while the illuminators were off. A second shortcoming of the prior art is that most of the techniques require a relatively large memory to store the images and the processing algorithms. Finally, many of the techniques are difficult or impossible to use with video cameras.

There is a need for an image subtraction technique which overcomes these shortcomings of the prior art. This system would be particularly useful to identify users of automated teller machines as well as individuals seeking access to a restricted area or facility or other applications requiring user identification. However, for such use to be commercially successful, there must be a rapid, reliable and unobtrusive way to obtain iris images of sufficient resolution to permit verification and recognition from an ATM user standing in front of the teller machine, and for the obtaining images of the subjects themselves to enable automatic iris image acquisition. To require the user to position his head a predetermined distance from the camera, such as by using an eyepiece or other fixture or without fixturing is impractical. Hence, the system must rapidly take and process the images so as to eliminate effects caused by movement of the subject.

SUMMARY OF THE INVENTION

We provide a method of image subtraction in which we first take a series of frames of a subject using a video camera such that each frame will contain an interlaced even field and odd field of raster lines. We illuminate the subject in a manner so that illumination is alternately on then off for the two successive fields of an image frame. Then we grab a single frame and take an absolute difference between the odd field and the even field. This resulting absolute difference image will represent the subject as illuminated by the system illumination only, and not by any ambient illumination, so that the image can be used to identify the subject in the image.

BRIEF DESCRIPTION OF THE FIGURES

FIG. 3 is an image similar to FIG. 2 taken while an illuminator was on.

FIG. 7 is an image of a subject similar to FIG. 2 taken while an illuminator was on.

BRIEF DESCRIPTION OF THE PREFERRED EMBODIMENTS

Figure 1:
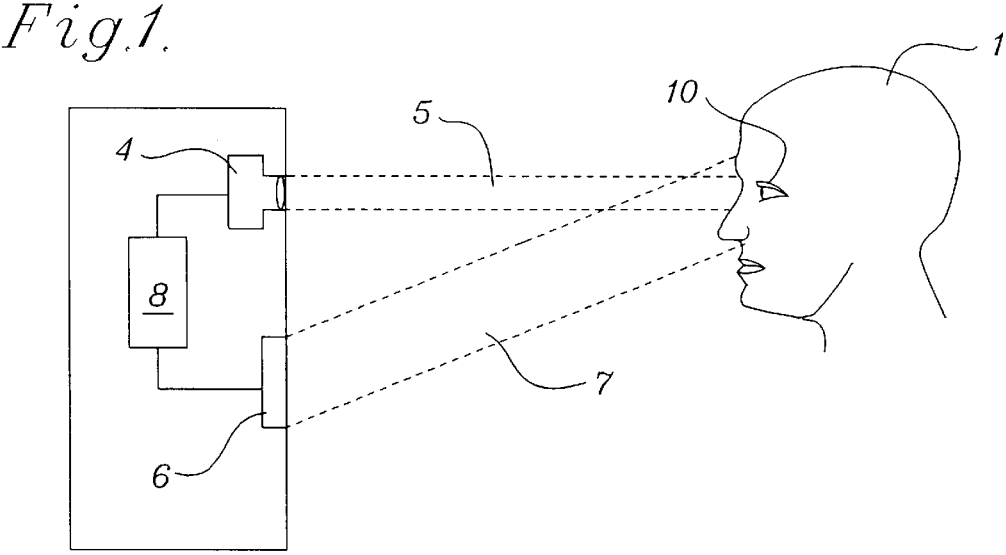
FIG. 1 is a diagram showing a subject of whose eye an image is taken with and without illumination.

Referring to FIG. 1 we provide a video camera in housing 2 to take an image of the eye 10 of the subject 1. The camera is positioned so that the eye 10 of the subject 1 is within the field of view 5 of the camera. The housing also contains at least one illuminator 6 and a controller 8. The controller may be a program contained in a computer which also contains programs and memory for performing image subtraction and image analysis. The illuminator directs a light beam 7 onto the area which is being photographed. We prefer to use an infrared light source and an infrared camera. The controller synchronizes the camera and illuminator so that successive picture fields will be alternately illuminated and not illuminated. The video camera will produce a series of field sub-images such as are shown in FIGS. 2 and 3, if one were to de-interlace the even and odd field of an image frame.

Figure 5:
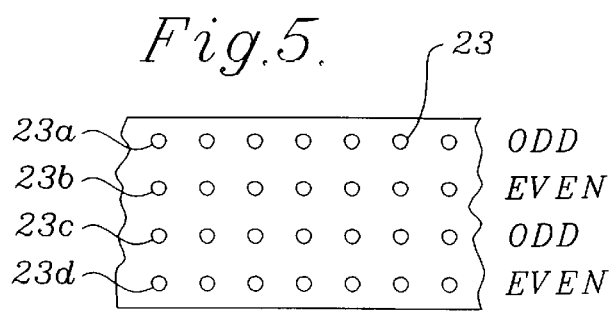
FIG. 5 is a diagram showing a small portion of a video image.

Normal video image frames are made up of a series of raster lines or fields indicated by lines 13. Each raster line is comprised of a set of pixels 23 as shown in FIG. 5. The fields are grouped according to odd and even raster lines. In the frame shown in FIG. 5, either all of the even field pixels are illuminated by the system illumination and the odd field pixels are not, or vice-versa. In either case, both even and odd fields are illuminated by ambient illumination.

Figure 2:
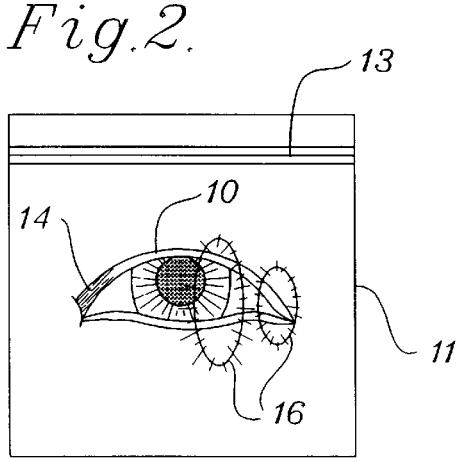
FIG. 2 is an image taken under ambient conditions.
Figure 3:
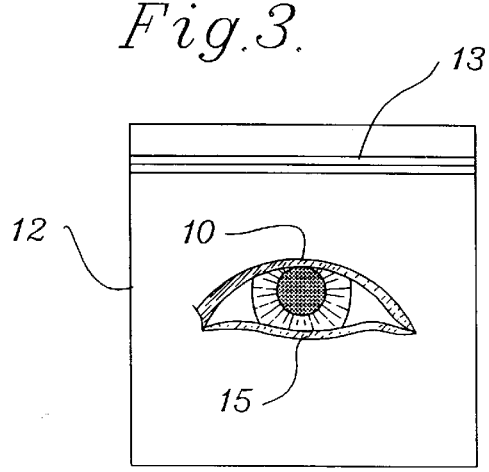
Figure 4:
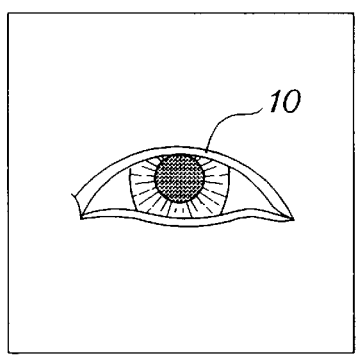
FIG. 4 is an image taken under illuminated conditions which has been corrected to remove the effects of ambient illumination.

The image of FIG. 2 was created while the illuminator was off. Ambient lighting conditions have created shadows 14 and bright spots indicated by regions 16. In the frame of FIG. 3 the illuminator was on creating an evenly lit image, although some areas 15 such as the eyelids may be darker than others. In order to properly identify the subject it is necessary to remove the effects of the ambient lighting to create an image without shadows or bright spots as shown in FIG. 4. We have developed an image subtraction method to rapidly remove the effects of ambient lighting.

In our method we take a single frame and subtract the pixel values in one field from the pixel values in the other field. Then we use the absolute value of that difference as the pixel's actual intensity had it been imaged with only system illumination. The subtraction is done between adjacent pixels. For example, in the region shown in FIG. 5 pixel 23a would be subtracted from pixel 23b and pixel 23c would be subtracted from pixel 23d. Alternatively pixel 23b could be subtracted from pixel 23a and pixel 23d could be subtracted from pixel 23c. Since we are using the absolute value rather than the straight difference it does not matter which of the two fields is subtracted from the other.

After we have performed image subtraction in this manner we will have a set of values that represents the original subject had it been imaged with system illumination but without ambient illumination, effectively removing the unwanted effects of ambient illumination. After this process a corrected image such as is shown in FIG. 4 will have been created. If the corrected image is that of the eye or iris of an person to be identified the corrected image is then used for identification using the techniques described in U.S. Pat. No. 4,641,349 to Flom et al. and U.S. Pat. No. 5,291,560 to Daugman.

Figure 6:
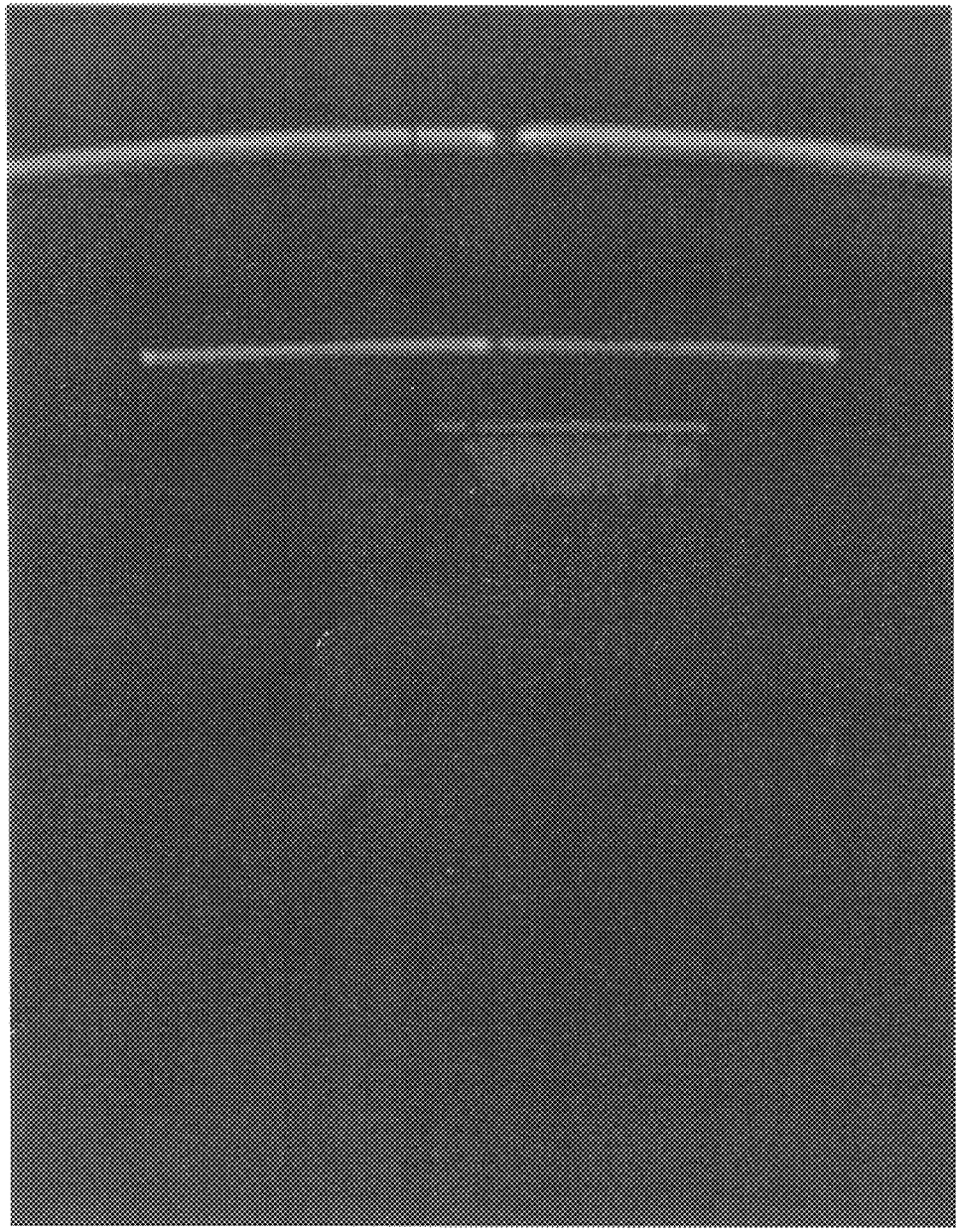
FIG. 6 is an image of a subject taken under ambient conditions.
Figure 7:
Figure 8:
FIG. 8 is an image of a subject taken under illuminated conditions which has been corrected to remove the effects of ambient illumination.

The image of FIG. 6 was created while the illuminator was off. The overhead lighting can distract and confuse algorithms designed to locate the subject's eye in 3-D space. In the frame of FIG. 7 the illuminator was on, clearly illuminating the subject. In order to properly locate the subject's eye it is necessary to remove the distracting effects of the background lighting as shown in FIG. 8. This method of image subtraction can also be used to rapidly remove the effects of background lighting and greatly facilitate the process of automatic iris image acquisition.

Since our method uses only a single frame it has several advantages. First it does not matter which frame is selected by the frame grabber. Furthermore, we do not require the capture of only one frame with the illumination on and one frame with the illumination off which would require that frame capturing be done at video rates. We also do not care which field is illuminated so long as one field is illuminated and one field is not. Hence, synchronization of the frame grabber with the camera is easier.

Another advantage of our method is that we need only store a single frame in memory so only half as much memory is needed than is required for conventional image subtraction. This is significant because each frame is 640× 480 pixels and each pixel has a gray scale value. Using one image also reduces the time during which the image must be stored.

Another implementation can reduce the time and memory requirements further by half by storing only the first field in memory and performing the absolute difference of the corresponding pixel values of the second incoming video field as it is being digitized, without requiring intermediate storage of the full second incoming field.

Our method can be used with any type of video camera. However, we prefer to use a CMOS (complementary metal-oxide semiconductor) imaging device. CMOS imagers have much more isolation between adjacent pixels than do charge coupled devices (CCD) which are commonly used. As a result in this type of imager there is no blooming which is the distortion of the values of pixels adjacent to those which receive bright light.

While we have described and shown certain present preferred embodiments of our method it should be distinctly understood that our invention is not limited thereto but may be variously embodied within the scope of the following claims.

We claim:

1. A method of image subtraction comprising the steps of:
   a. taking a series of frames of a subject using a video camera such that each frame will contain an even field of raster lines and an odd field of raster lines;
   b. illuminating the subject in a manner so that illumination is alternately on then off for successive fields to create at least one frame in which one of the even field of raster lines and the odd field of raster lines was created with the illumination off and the other of the even field of raster lines and an odd field of raster lines was created with the illumination on;
   c. grabbing a single frame in which one of the even field of raster lines and the odd field of raster lines was created with the illumination off and the other of the even field of raster lines and the odd field of raster lines was created with the illumination on; and
   d. finding an absolute difference between the odd field and the even field in said single frame thereby creating a representation of the subject illuminated by system illumination without ambient illumination.

2. The method of claim 1 also comprising:
   a. acquiring a next frame having an odd field of raster lines and an even field of raster lines, and
   b. computing an absolute difference between the even field of one of the single frame and the next frame and the odd field of the other of the single frame and the next frame to create a corrected image.

3. The method of claim 1 wherein the illumination is performed using an infrared light source.

4. The method of claim 1 wherein the camera is a CMOS device.

5. The method of claim 1 wherein the image subtraction is performed by a computer.

6. The method of claim 1 wherein only a single frame is stored in memory.

7. The method of claim 1 wherein the grabbed frame includes an image of an iris of the subject and also comprising the step of applying at least one iris identification algorithm to at least a portion of the representation of the subject.

8. The method of claim 1 wherein the grabbed frame includes an image of a subject and also comprising the step of applying an automatic iris acquisition algorithm to at least a portion of the representation of the subject.

* * * * *